United States Patent [19]

Shipko et al.

[11] 4,316,471
[45] Feb. 23, 1982

[54] ORGAN STIMULATING APPARATUS WITH SEALING SETSCREW

[75] Inventors: Frederick J. Shipko, Spring Church; Robert D. Norman, Indiana, both of Pa.

[73] Assignee: Coratomic, Inc., Indiana, Pa.

[21] Appl. No.: 151,379

[22] Filed: May 19, 1980

[51] Int. Cl.³ .............................................. A61N 1/00
[52] U.S. Cl. .................................................. 128/419 P
[58] Field of Search ........ 128/419 P, 419 PG, 419 PS

[56] References Cited

U.S. PATENT DOCUMENTS

| 4,010,760 | 3/1977 | Kraska et al. | 128/419 P |
| 4,037,277 | 7/1977 | Shipko | 128/419 P |
| 4,141,752 | 2/1979 | Shipko | 128/419 P |

*Primary Examiner*—William E. Kamm
*Attorney, Agent, or Firm*—Hymen Diamond

[57] ABSTRACT

A heart pacemaker including a captive sealing setscrew for securing and preventing leakage of body fluids to the catheter. The setscrew has a head of a material of high tensile strength, stiffness, resiliency, toughness and fatigue endurance, typically Delrin. The head is cylindrical but has a circumferential projection at its inner end. The pacemaker includes an internally threaded receptacle which is engaged by the setscrew as the setscrew is advanced to secure the catheter. Externally of this receptacle there is a sleeve of silicone rubber. At the outer end of the rubber sleeve there is a recess. Inwardly of the recess the rubber sleeve is of smaller internal diameter than the projection so that when the screw is screwed into the receptacle, a tight seal to prevent penetration of body fluids is formed by the projection and sleeve. The recess has a greater diameter than the projection but has an outwardly extending lip of smaller diameter than the maximum diameter of the projection but of greater diameter than the remainder of the head. The screw can be disengaged from the threaded sleeve but its ready release from the rubber sleeve is prevented.

The setscrew is screwed in by a screwdriver also of Delrin which has a substantially lower torque resistance than the head of the setscrew so that the setscrewdriver twists out of shape before enough torque can be applied to the head to damage it.

17 Claims, 9 Drawing Figures

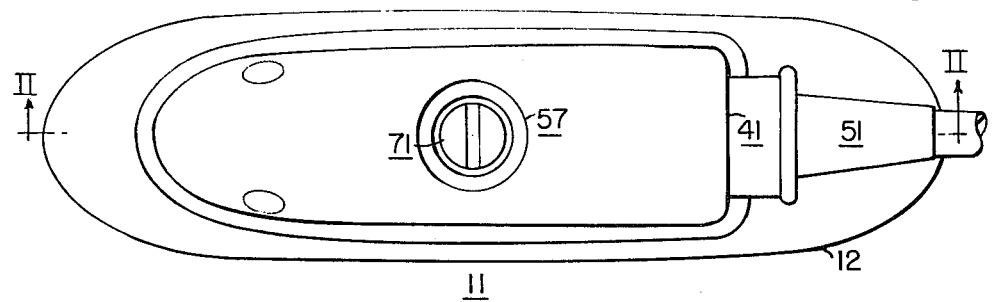
FIG.1
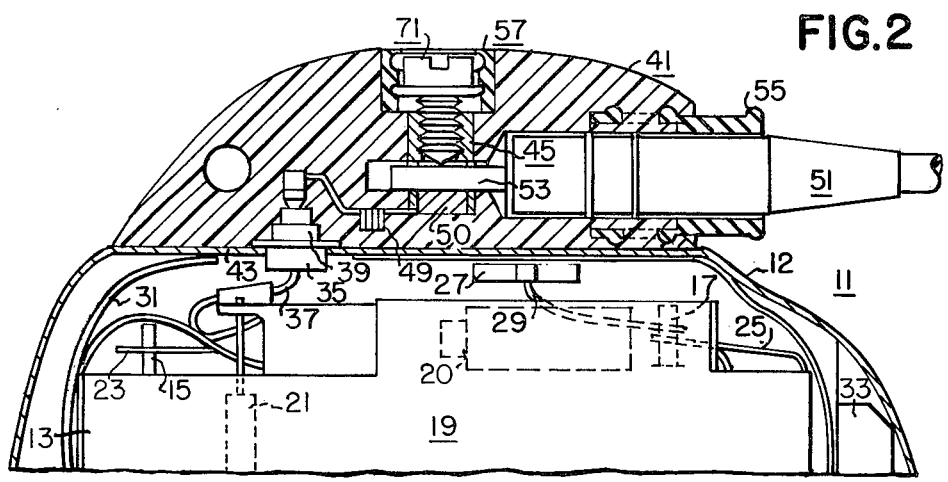
FIG.2
FIG.3
FIG.4

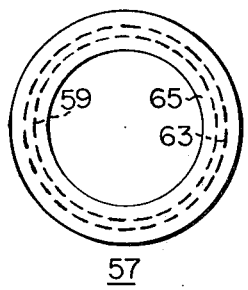
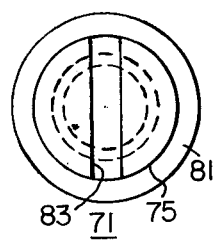
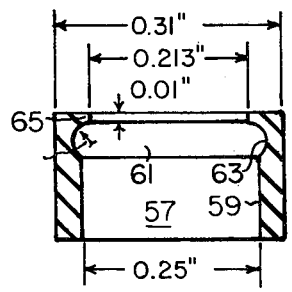
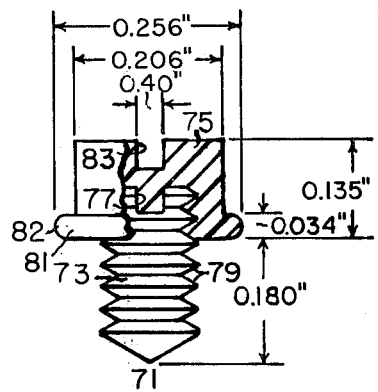
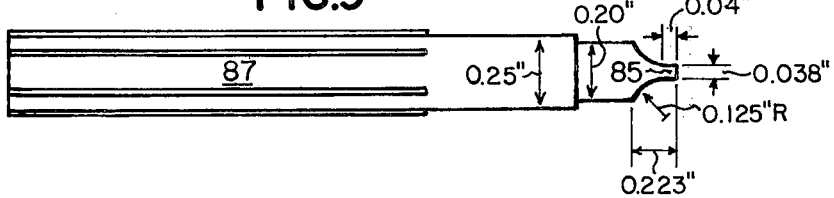

ORGAN STIMULATING APPARATUS WITH SEALING SETSCREW

BACKGROUND OF THE INVENTION

This invention relates to organ-stimulating apparatus and has particular relationship to such apparatus having a catheter, which is secured in the apparatus by a setscrew unit and serves to transmit stimulation to the organ. An important demand imposed on this setscrew is that it seals the apparatus tightly against penetration of body fluids to the catheter. The setscrew is a relatively small object and is secured to the catheter during a surgical operation. It has been found desirable, for the purpose of precluding the loss of the setscrew on the operating table or elsewhere in the operating room, to maintain the setscrew in the organ-stimulating apparatus ready for use. To achieve this object it has been proposed that the setscrew be held in the channel where it is to be screwed in to secure the catheter by a self-sealing plug or silastic rubber. The plug also is intended to serve to prevent penetration of body fluids. This expedient has the disadvantage that it demands that the instrument for screwing in the setscrew be manipulated without seeing the head of the setscrew. It can readily happen that the setscrew is not properly screwed in and damages the thread which it is to engage without securing the catheter. In addition, the self-sealing plug is not entirely reliable in preventing the penetration of body fluids.

U.S. Pat. No. 4,141,752 granted Feb. 27, 1979 to Frederick J. Shipko for ORGAN STIMULATING APPARATUS AND INSULATING SET SCREW FOR SUCH APPARATUS (herein called Shipko) is typical of other prior art. In Shipko the catheter is secured by a setscrew around whose head an O-ring extends. The O-ring has a greater diameter than the well into which the head extends. The O-ring serves to retain the setscrew in the organ-stimulating apparatus before it is screwed in to engage the catheter and also to seal the apparatus against the penetration of body fluids. While this apparatus has operated reasonably satisfactorily, surgeons who have used it have demanded that the setscrew be held captive more positively. Shipko's setscrew also has a metallic strengthening cap embedded in a plastic head. Some surgeons have objected to this feature.

It is an object of this invention to overcome the drawbacks and disadvantages of the prior art and to provide organ-stimulating apparatus in which the setscrew, which secures the catheter, shall both effectively seal the apparatus against leakage of body fluids and be positively held captive while lending itself to ready manipulation.

It is another object of this invention to provide such a setscrew which, while uniquely suitable as a component of organ-stimulating apparatus, has general applicability.

SUMMARY OF THE INVENTION

In accordance with this invention organ-stimulating apparatus is provided which includes a receptacle, transversely to the channel into which the catheter is inserted, to receive the setscrew for securing the catheter. Externally to and coextensive with the receptacle, this apparatus includes a resilient member typically composed of silicone rubber which is biocompatible with the body. This member has a recess near its external end. The setscrew has a plastic head. Inwardly of the recess the resilient member has an inner transverse dimension which is smaller than the maximum transverse dimension of the head. This relationship exists throughout the whole periphery of the head and resilient member. When the setscrew is screwed into the receptacle, the organ stimulating apparatus is tightly sealed against penetration of body fluids at the junction of the head and resilient member. The recess has a transverse dimension greater than the maximum transverse dimension of the head. The recess is terminated by a lip which defines an opening near the end of the resilient member. This opening has a transverse dimension smaller than the maximum transverse dimension of the head but permits the outer portion of the head, of smaller transverse dimension that the maximum, to penetrate outwardly. When the setscrew is disengaged from the receptacle, this portion of the head extends through the opening defined by the lip and is readily manipulated, but the setscrew cannot fall out from the apparatus into the patient's body or to the floor, because the portion of the head of maximum dimension abuts against the lip.

BRIEF DESCRIPTION OF THE DRAWINGS

For a better understanding of this invention, both as to its organization and as to its method of operation, together with other objects and advantages thereof, reference is made to the following description, taken in connection with the accompanying drawings, in which:

FIG. 1 is a plan view of organ-stimulating apparatus, specifically a heart pacemaker, in accordance with this invention;

FIG. 2 is a view in section taken along line II—II of FIG. 1, with the catheter unsectioned, showing only the upper portion of the heart pacemaker;

FIG. 3 is a fragmental view in longitudinal section showing the setscrew unit included in the apparatus shown in FIGS. 1 and 2 with the setscrew in engagement with the catheter;

FIG. 4 is a fragmental view similar to FIG. 3 but with the setscrew completely retracted from the receptacle;

FIG. 5 is a plan view of the resilient member included in the apparatus shown in FIGS. 1 and 2;

FIG. 6 is a view in section taken along lines VI—VI of FIG. 5;

FIG. 7 is a plan view of the setscrew included in the apparatus shown in FIGS. 1 and 2;

FIG. 8 is a view in section taken along line VIII—VIII of FIG. 7, and

FIG. 9 is a view in side elevation of the screw driver used to screw in the setscrew in the practice of this invention.

The use of the heart pacemaker as illustrative of this invention is intended only as an aid to the understanding of this invention and should not in any way limit the scope of this invention. Likewise, the presentation of dimensions in FIGS. 5 through 9 is intended only as an aid to those skilled in the art to understand the practice of this invention and should not in any way limit the scope of this invention.

DETAILED DESCRIPTION OF EMBODIMENT

The apparatus shown in FIGS. 1 and 2 includes a heart pacemaker 11. The pacemaker 11 includes a sealed container 12 of ovaloidal or ellipsoidal form similar to the container of U.S. Pat. No. 3,987,799 and of Shipko. The container is typically composed of titanium. The pacemaker is powered by a long-life lithium battery 13 within the container 12 having terminals 15 and 17. The power from the battery 13 is converted by a hybrid circuit 19, into pulses whose intervals may be selectively programmed. The hybrid circuit 19 includes capacitors 20 (only one shown). The programming is effected by an external programmer (not shown) through reed switches 21 (only one shown), appropriately connected to the hybrid circuit 19. The battery terminals 15 and 17 are interconnected with the hybrid circuit by electrically conductive strips 23 and 25. The ground terminal for the hybrid circuit is provided by an electrically conductive strip 27 which is itself conductively connected to the wall of container 12. The strip 27 is connected to the ground terminal 17 of the battery by electrical conductor 29.

The container 12 is composed of complimentary halves which are welded by a laser beam. The internal components of the pacemaker 11 are protected from the heat of the laser beam by a laser shield 31.

Within the container 12 but outside of the laser shield there is a plate 33 which bears identification so tha the maker and type of the pacemaker 11 can be determined from an X-ray film of the host.

The pacemaker 11 has a feedthrough 35 sealed through the container 12. The output conductor 37 which carries the pulses from the hybrid circuit 19 is sealed through the feedthrough 35, and connected to an output terminal 39 on the pacemaker 11.

The pacemaker 11 includes a capsule 41 typically of epoxy resin or the like. The capsule extends from and is sealed to the wall 43 of the container 12 through which the feedthrough 35 is sealed and embeds the external portion of the feedthrough 35 and the terminal 39. A terminal block or receptacle 45, which is typically square, is embedded generally centrally in the capsule. The block 45 includes an internal thread 47. The block 45 is connected to the terminal 39 by a conductor 49 which is also embedded in the capsule 41. The block 45 is closed at its inner end by a plug 50 to prevent the penetration of epoxy into the block.

The capsule 41 is provided with a channel for receiving a catheter 51 having a terminal 53. The terminal 53 may be of different cross-sectional dimensions. The channel extends transversely of the block 45 and is attenuated in the region through which the terminal 53 passes. The block 45 has a transverse opening to receive the terminal 53. The opening is coaxial with the attenuated region. Within the capsule 41 the catheter is firmly engaged by a grommet 55, the inner portion of which is embedded in the capsule 41.

A well extends into the capsule 41 externally of and coextensive with the receptacle 45. The inner diameter of the well is greater than the outer diameter of the receptacle 45. A resilient sleeve 57 (FIGS. 5, 6) is cemented into the well. The sleeve is formed by molding and is composed of silicone rubber compatible with human tissue typically Dow corning MDX-4-4515 or Medical Engineering Co. MEC-501. The dimensions and form of the sleeve 57 are shown in FIGS. 5 and 6. Inwardly of the pacemaker 11, the internal surface 59 of the sleeve 57 is circularly cylindrical. This surface 59 merges into a recess 61 near the outer end of the sleeve 57. The internal surface 63 of the recess 61 is of arcuate section and its maximum diameter is greater than the diameter of the surface 59. The recess 61 terminates in a lip 65 at the end of the resilient sleeve 57. The diameter of the opening in the lip is smaller than the diameter of cylindrical surface 59.

The apparatus also includes a setscrew 71. The setscrew 71 has a threaded member 73 to which a plastic head 75 is molded. The threaded member 73 is typically composed of titanium; the head 75 is typically composed of DuPont Delrin 150. This material is the highest molecular-weight plastic available. The material is generally referred to as an acetal and is a homopolymer of formaldehyde gas. This material has high tensile strength, high resiliency, high toughness and long fatigue endurance. The threaded member 73 has a diametral slot 77. This slot provides reinforcement for attachment of the plastic head 75 and prevents the head 75 from turning in the thread 79 of the threaded member 73 which it engages when the screw 71 is turned against resistance. Near or at its lower end, the head 75 has a circumferential projection 81 whose outer surface 82 is of arcuate section. The head also has a diametral slot 83 for engagement of the tip 85 of the screw driver 87 (FIG. 9). The dimensions of the setscrew 71 are presented in FIG. 8. The setscrew 71, the threaded receptacle 45, and the resilient sleeve 57 constitute what may be described as a setscrew unit.

The maximum diameter of the projection 81 is greater than the diameter of the surface 59 of the resilient sleeve 57. The material of the sleeve 57 is yieldable so that when the setscrew is screwed into the threaded receptacle 45, the projection 81 firmly engages and compresses the material of the sleeve 57 at the surface 59 as shown in FIG. 3. The material of the resilient sleeve 57 envelopes the end of the surface 82 of the projection 81 forming a sound tight seal which is not penetrable by body fluids. The maximum diameter of the surface 63 of the cavity 61 is greater than the maximum diameter of the projection 81 and the radius of the surface 82 is slightly smaller than the radius of the surface 63, so that when the setscrew is retracted from the receptacle 45, the projection 81 nests loosely in the cavity 61 as shown in FIG. 4. The diameter of the opening in the lip or overhang 64 is smaller than the maximum diameter of the projection 81 but is greater than the diameter of the upper portion of the head 75 of the setscrew 71. The setscrew 71 is held captive in the resilient sleeve 57 but, as shown in FIG. 4, may be readily manipulated.

The setscrew 71 is inserted in pacemaker 11 before the pacemaker is shipped or before it is used. In inserting the setscrew 71, the setscrew is held at an angle to the opening in the lip 65 and one end of the projection 81 is nested in the cavity 61. Then the remainder of the projection 81 is inserted in the cavity 61 by deflecting the necessary portion of the lip 65 and pressing the remainder of the projection through the depressed lip portion. The setscrew 71 is then in the position shown in FIG. 4 held positively captive by the resilient member 57 but readily engageable with the thread 47 in the receptacle 45. The material of which the head 75 is composed has a low coefficient of friction so that the insertion in the resilient sleeve 57 is facilitated.

The screwdriver 87 is provided with each pacemaker 11 to operate the setscrew 71 of that pacemaker. The screwdriver 87 is composed of the same material as the head 75 of the setscrew 71 (DuPont Derin 150). The dimensions of this screwdriver are such that it becomes twisted at a lower torque than that at which the heat 75 would be damaged. Typically about 4 or 5 foot pounds of torque are required to fracture the head 75; the screwdriver 87 twists out of shape for 0.4 or 0.5 foot pounds of torque.

While a preferred embodiment of this invention has been disclosed herein, many modifications thereof are feasible. It is to be borne in mind that while the setscrew-captive feature of this invention is an important significant advance in the art, the sealing effected by the resilient sleeve 57 in itself constitutes an important advance in the art. Organ stimulating apparatus including the resilient sleeve 57 but not the cavity 61 or the resilient sleeve 57 alone with an overhang or lip at the outer end to retain the setscrew is within the scope of this invention. The diameter of the head 75 of the setscrew 71 may vary continuously instead of having the projection 81 or, in some cases, may be constant but greater than the inner diameter of the resilient sleeve 57. This invention is not to be restricted except insofar as is necessitated by the prior art.

We claim:

1. Organ-stimulating electrical apparatus to be implanted in a body including a catheter for connecting said apparatus to an organ of said body, the said catheter to extend into said apparatus and to be electrically connected thereto, said apparatus also including a threaded receptacle extending into said apparatus generally laterally of said catheter, a resilient member extending into said apparatus coextensive with said receptacle and a setscrew for securing said catheter in said apparatus, the said setscrew including:
   (a) a threaded member for screwing into the thread of said receptacle and engaging and securing said catheter; and
   (b) a head secured to said threaded member, the maximum transverse dimension of said head being greater than the transverse dimension of at least the portion of said resilient member which is engaged by said head, throughout the peripheries of said head and portion, when said threaded member is screwed into said receptacle into securing engagement with said catheter, so that when said threaded member is so screwed into said receptacle, the engagement of said resilient member by said head seals the region of said apparatus extending inwardly of said head against the penetration of body fluids.

2. The apparatus of claim 1 wherein the portion of the resilient member whose transverse dimension is less than the maximum transverse dimension of the head terminates, remotely from the threaded member, in a recess whose transverse dimension is greater than the maximum transverse dimension of the head, said recess including means for preventing the release of said setscrew from said resilient member.

3. The apparatus of claim 2 wherein the head includes a peripheral projection extending from the head near the innermost region of the head and the release preventing means includes a lip overhanging the recess near its outermost region, the transverse inner dimension of the opening in said lip being smaller than the outer transverse dimension of the projection but greater than the transverse dimension of the remainder of the head, so that when the threaded member is screwed out of the receptacle, the head extends out of the lip but is prevented by its projection from being released from the resilient member.

4. The apparatus of claim 1 wherein the head includes a peripheral projection extending outwardly of the head which defines the maximum transverse dimension of said head.

5. The apparatus of claim 1 wherein an overhang or lip is provided near the outermost end of the resilient member, the transverse dimension of said lip being smaller than the maximum transverse dimension of the head but greater than transverse dimension of said head which is smaller than said maximum transverse dimension.

6. Organ stimulating electrical apparatus to be implanted in a body including a catheter for connecting said apparatus to an organ of said body, said apparatus including a channel into which said catheter is to extend and whereby said catheter is to be electrically connected to said apparatus, said apparatus also including an internally threaded receptacle extending into said apparatus in communication with said channel, a resilient sleeve extending into said apparatus coextensive with said threaded receptacle externally of said threaded receptacle and a setscrew for securing said catheter in said apparatus, said setscrew including:
   (a) a threaded member for screwing into said thread of said threaded receptacle and engaging said catheter to secure it; and
   (b) a head secured to said threaded member, the maximum diameter of said head being greater than the diameter of at least that portion of said resilient sleeve which is engaged by said head when said threaded member is screwed into said thread of said threaded receptacle into securing engagement with said catheter, so that when said threaded member is so screwed into said receptacle, the engagement of said resilient sleeve by said head seals the region of said apparatus extending inwardly of said head against the penetration of body fluids.

7. The apparatus of claim 6 wherein the head has a radially outwardly extending projection which defines its maximum diameter.

8. The apparatus of claim 6 wherein the resilient sleeve includes a recess, outwardly of the portion of said sleeve, the said recess being contiguous to said portion and including a first region of greater internal diameter than the maximum diameter of the head and a second region outwardly of said first region whose internal diameter is less than the maximum diameter of said head so that on disengagement of said setscrew from securing engagement with the catheter, the release of said setscrew from said resilient sleeve is prevented.

9. The apparatus of claim 8 wherein the head includes a projection extending radially outwardly from the head near the innermost region of the head and the second region is a lip overhanging the recess near its outermost region, the diameter of the opening in said lip being smaller than the outer diameter of said projection but greater than the remainder of said head, so that when the threaded member is screwed into the threaded receptacle, the head extends out of the lip but is prevented from being released from the resilient sleeve.

10. A sealing setscrew unit including a setscrew including a threaded member and a head extending from said threaded member, a receptacle internally threaded, its thread to be engaged by said threaded member, a resilient member coextensive with, and outwardly of, said receptacle with respect to said threaded member so as to be engaged by said head, the maximum transverse dimension of said head being greater than at least that portion of the resilient member which is engaged by said head when said threaded member is screwed into said receptacle, throughout the peripheries of said head and resilient member so that when said head engages said resilient member, it seals the region outwardly of said head with respect to said threaded member from the region inwardly of said head with respect to said threaded member.

11. The setscrew unit of claim 10 wherein the resilient member includes a recess outwardly of said resilient member with respect to said threaded member, said recess including a first region whose transverse dimension is greater than the maximum transverse dimension of said head and a second region outwardly of said first region with respect to said threaded member, whose transverse dimension is less than the transverse dimension of said first region so that when said threaded member is disengaged from said receptacle, it is prevented from being released from said resilient member by said second region.

12. The setscrew unit of claim 10 wherein the head includes, near its innermost end with respect to said threaded member, a peripheral projection which defines its maximum transverse dimension.

13. The setscrew unit of claim 12 wherein the second region of the recess has an opening whose transverse dimension is greater only than that portion of the head which is outwardly, with respect to the threaded member, of the projection.

14. The setscrew unit of claim 10 wherein the resilient member is a circularly cylindrical sleeve of resilient material and the head is circularly cylindrical having a circular projection near its innermost end with respect to the threaded member.

15. For use in securing a catheter to organ stimulating apparatus, the combination of a setscrew and a screwdriver, said setscrew having a threaded member and a head, said apparatus having a receptacle to be engaged by said threaded member, said head having slot means and said screwdriver having a tip to engage said slot means to turn said threaded member in said receptacle into engagement with said catheter, the torque-resistant strength of said screwdriver being substantially less than the torque-resistant strength of said head, so that said screwdriver will twist out of shape to prevent excessive torque impressed on it from damaging said head.

16. The combination of claim 15 wherein the head is composed of a plastic material and the screwdriver is composed of the like plastic material in the region where it is subjected to maximum stress by the torque applied in screwing the threaded member into the receptacle, said screwdriver being of substantially smaller cross-sectional dimension than the head where it is subjected to maximum stress.

17. The combination of claim 16 wherein the plastic material is a homopolymer made from formaldehyde gas generally referred to as an acetal and sold by DuPont under the name Delrin 150.

* * * * *